: US005674720A

United States Patent [19]
Gorelick et al.

[11] Patent Number: 5,674,720
[45] Date of Patent: Oct. 7, 1997

[54] DESIGN AND CONSTRUCTION OF NON-INFECTIOUS HUMAN RETROVIRAL MUTANTS DEFICIENT IN GENOMIC RNA

[75] Inventors: Robert J. Gorelick, Braddock Heights; Larry O. Arthur, Walkersville; Alan Rein, Takoma Park; Louis E. Henderson, Mount Airy; Stephen Oroszlan, Potomac, all of Md.

[73] Assignee: United States of America, Washington, D.C.

[21] Appl. No.: 176,682

[22] Filed: Jan. 3, 1994

Related U.S. Application Data

[63] Continuation of Ser. No. 429,287, Oct. 31, 1989, abandoned, which is a continuation-in-part of Ser. No. 269,407, Nov. 10, 1988, abandoned.

[51] Int. Cl.$^6$ .............................. C12N 13/00; C12P 21/06; C07K 1/00; A61K 39/21
[52] U.S. Cl. ..................... 435/172.3; 435/69.1; 530/350; 530/395; 424/208.1; 424/204.1; 424/188.1
[58] Field of Search .................................. 424/89, 188.1, 424/204.1, 184.1; 530/350, 395; 435/69.1, 172.1

[56] References Cited

FOREIGN PATENT DOCUMENTS

WO105860   5/1991   WIPO.

OTHER PUBLICATIONS

Gorelick, et al. 'Point Mutants of Moloney murine leukemia virus that fail to package viral RNA: Evidence for specific RNA recognition by a "zinc finger–like" protein sequence', Proceedings Of The National Academy of Sciences of USA, vol. 85, No. 22, Nov. 1988, pp. 8240–8424.

Meric, et al. "Characterization of Moloney Murine Leukemia Virus Mutants with Single–Amino–Acid Substitutions in the Cys–His Box of the Nucleocapsid Protein", Journal of Virology, vol. 63, No. 4, Apr. 1989, pp. 1558–1568.

Aldovini, et al. 'Mutations of RNA and Protein Sequences Involved in Human Immunodeficiency Virus Type 1 Packaging Result in Production of Noninfectious Virus', Journal of Virology, vol. 64, No. 5, May 1990, pp. 1920–1926.

Carlson et al. "Vaccine Protection of Rhesus Macaques Against Simian Immuodeficiency Virus Infection", AIDS Research And Human Retroviruses, vol. 6, No. 11, 1990.

Desrosiers et al. "Vaccine Protection Against Simian Immunodeficiency Virus Infection", Proc. Natl. Acad. Sci. USA, vol. 86, pp. 6353–6357, Aug. 1989, Medical Sciences.

Murphey–Corb et al. "A Formalin–Inactivated Whole SIV Vaccine Confers Protection in Macaques", Science, vol. 246, 8 Dec. 1989, Reports 1293.

Morrison et al. "Different H–2 Subregions Influence Immunization Against Retroviruses and Immunosuppression", Nature, vol. 329 22 Oct. 1987, p. 729.

Mann et al. "Construction of a Retrovirus Packaging Mutant and Its Use to Produce Helper—Free Defective Retrovirus", Cell., vol. 33, 153–159, May 1983.

Gorelick et al. "Noninfectious Human Immunodeficiency Virus Type 1 Mutants Deficient in Genomic RNA", Journal of Virology, Jul. 1990, pp. 3207–3211.

Henderson et al. "Primary Structure of the Low Molecular Weight Nucleic Acid–Binding Proteins of Proteins of Murine Leukemia Viruses", The Journal of Biological Chemistry, vol. 256, No. 161, Aug. 25, pp. 6400–6406; 1981.

Covey, "Amino Acid Sequence Homology in GAG Region of Reverse Transcribing Elements and the Coat Protein Gene of Cauliflower Mosaic Virus", Nucleic Acids Research, vol. 14, No. 2, 1986, pp. 623–633.

Berg, "Potential Metal—Binding Domains in Nucleic Acid Binding Proteins", Reports, 25 Apr. 1986 (Dept of Biophysics, Johns Hopkins University School of Medicine), pp. 485–487.

Meric et al. Mutations in rous sarcona virus nucleocapsid protein, p. 12 . . . 1988, Journal of Virol. vol. 62(9): 3328–3333.

Meric et al, 1986, J. Virol. 49(3): 909–917.

Zoller et al, 1982, Oligonncleotide–directed mutagenesis using M13. . . , Nucleic Acids Res. 10(20): 6487–6500.

Hsu et al, 1985, Point mutations in the P30 domain of the gag. . . , virology 142:211–214.

Crawford et al. 1984, Mutations in gag protein p12 and p15 . . . , Journal of Virology 49(3):909–917.

Meric, et al., "Site—Directed Mutagenesis of the Nucleocapsid P10 of Moloney Murine Leukem A Virus," p. 106, *Abstracts of Papers Presented at the 1988 Meeting on RNA Tumor Viruses*, Cold Spring Harbor, NY.

(List continued on next page.)

*Primary Examiner*—Lynette F. Smith
*Attorney, Agent, or Firm*—Townsend and Townsend and Crew LLP

[57] ABSTRACT

The present invention defines a biological role for the following sequence of amino acids that is found in the nucleocapsid domain of the gag precursor polyproteins of all replication-competent retroviruses:

-Cys-X-X-Cys-X-X-X-X-His-X-X-X-X-Cyswherein X represents variable amino acids. The invariant residues constitute part of a vital protein structure, at least one of which are found in all retroviruses and which are involved in the selection and packaging of genomic viral RNA into infectious virus particles. Disruption of this structure leads to the formation of virus-like particles which appear to be structurally normal, but which do not contain the normal complement of viral RNA. Therefore, their infectivity is drastically reduced or completely eliminated. The infectivity of any retrovirus, including human retroviruses, and more particularly human immunodeficiency virus (HIV), can be drastically reduced or completely eliminated by generating mutants that lack some or all of the invariant residues required to form the structure. In addition, any means of disrupting the function of this array will in turn disrupt the viral life cycle. Thus, with the knowledge provided by this invention, chemotherapeutic reagents aimed toward this array may be devised.

18 Claims, 7 Drawing Sheets

OTHER PUBLICATIONS

Gorelick, et al., "Point Mutations Preventing Encapsidation of Moloney HuLV RNA: Evidence for Role of 'Finger–Like' Sequence in Recognition of Genomic RNA," p. 107, *Abstracts of Papers Presented at the 1988 Meeting on RNA Tumor Viruses*, Cold Spring Harbor, NY.

Brown, 1993, "AIDS Vaccine Trials Viewed With Caution" Wash. Post Newspaper Jun. 10, 1993.

Greene, 1993, "AIDS and the Immune System", Scienctific American pp. 99–105, Sep. 1993 issue.

Meric, et al., 1986, J. Virol. 49(3): 909–917.

5,674,720

DESIGN AND CONSTRUCTION OF NON-INFECTIOUS HUMAN RETROVIRAL MUTANTS DEFICIENT IN GENOMIC RNA

This is a continuation of application Ser. No. 07/429,287, filed on Oct. 31, 1989, which was abandoned upon the filing hereof which is a continuation-in-part of application Ser. No. 269,407, filed Nov. 10, 1988 now abandoned.

BACKGROUND OF THE INVENTION

1. Field of the Invention

The present invention relates to the disruption of vital protein structures common to all retroviruses and involved in the selection and packaging of genomic vital RNA into infectious virus particles. More specifically, the present invention relates to the drastic reduction or complete elimination of the infectivity of any retrovirus, including human retroviruses, by the generation of mutants that lack some or all of the invariant residues required to form the structure. In one embodiment, the infectivity of human immunodeficiency virus (HIV) is drastically reduced or completely eliminated by the generation of such mutants.

2. Background Information

A virus particle is a "package" in which virus-coded proteins surround and protect the viral genome. Thus, the viral proteins must be able to specifically recognize and select the viral genome for "packaging" during virus assembly. Very little is known about the mechanisms involved in this recognition, although in the case of retroviruses, a noncoding sequence near the 5' end of the viral RNA is necessary (P. Shank et al. (1980) *J. Virol.* 36, 450–456; R. Mann et al. (1983) *Cell* 33, 153–159) but not sufficient (J. Sorge et al. (1983) *J. Virol.* 48, 667–675; S. Goff et al. (1987) *Biochem. Biophys. Acta* 907, 93–123) for efficient encapsidation of the RNA. One naturally occurring mutant of avian sarcoma virus which has apparently lost the ability to selectively encapsidate viral RNA has been described (M. Linial et al. (1978) *Cell* 15, 1371–1381), but the lesion in the viral proteins responsible for this defect has not yet been identified.

All retroviruses encode a polyprotein, termed the gag precursor, which plays a critical role in the virus assembly process. After virus assembly and release have occurred, the polyprotein is cleaved into the gag or core proteins found in the mature, infectious virus particle. One of these proteins, the "nucleocapsid" protein, binds nucleic acids in vitro and is believed to be associated with the genomic RNA in the virion. In all retroviruses, the nucleocapsid protein contains either one or two copies of the sequence:

-Cys-X-X-Cys-X-X-X-X-His-X-X-X-X-Cys- (L. Henderson et al. (1981) *J. Biol. Chem.* 256, 8400–8406; S. Oroszlan et al. (1985) *Current Topics in Microbiology and Immunology*, P. Vogt. ed., Springer-Verlag, New York, pp. 221–233; S. Covey (1986) *Nucl. Acids Res.* 14, 623–633). As previously described (J. Berg (1986) *Science* 232, 485–486), this sequence bears a striking resemblance to the "zinc finger" protein sequences implicated in recognition of specific DNA sequences by a wide variety of eukaryotic transcription factors (R. Evans et al. (1988) *Cell* 52, 1–3). However, zinc fingers have not been shown to interact with RNA.

The ubiquity of this motif in retroviral nucleocapsid proteins suggests that it performs an essential function in the viral life cycle, and its similarity to the "zinc fingers" raises the possibility that it is involved in the specific interaction with the viral genome which occurs during virus assembly. Accordingly, the present inventors tested the effects of mutations in this motif upon the infectivity of the virus and upon its ability to package genomic RNA. The results of these experiments, as set forth below, show that the motif is indeed involved in specific RNA recognition.

SUMMARY OF THE INVENTION

It is an object of the present invention to define a biological role for the following sequence of amino acids that is found in the nucleocapsid domain of the gag precursor polyproteins of all replication-competent retroviruses:

-Cys-X-X-Cys-X-X-X-X-His-X-X-X-X-Cyswherein X represents variable amino acids. The invariant residues constitute part of a vital protein structure, at least one of which are found in all retroviruses and which are involved in the selection and packaging of genomic viral RNA into infectious virus particles. Disruption of this structure leads to the formation of virus-like particles which appear to be structurally normal, but which do not contain the normal complement of viral RNA. Therefore, their infectivity is drastically reduced or completely eliminated.

It is thus another object of the present invention to drastically reduce or eliminate the infectivity of any retrovirus, including human retroviruses, and more particularly human immunodeficiency virus (HIV), by generating mutants that lack some or all of the invariant residues required to form the structure.

It is still another object of the invention to utilize said mutants in the design of vaccines.

It is yet another object of the invention to develop effective therapeutic agents utilizing said mutants.

It is still another object of the invention to develop diagnostic procedures for the detection of all infectious retroviruses.

DETAILED DESCRIPTION OF THE INVENTION

Figure 1A:
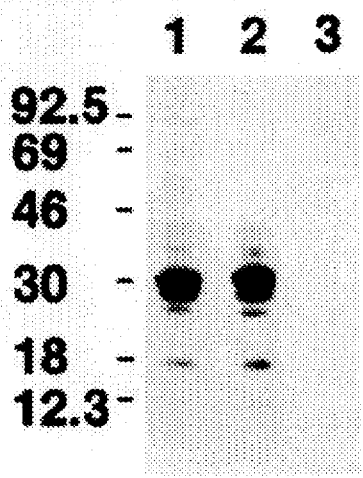
FIG. 1. Properties of viral mutants. (A) Protein immunoblotting. Virus was harvested from one 150 cm$^2$ flask containing 35 ml media and processed for protein immunoblotting, using antiserum against p30$^{gag}$. Lanes: 1, mutant C39S; 2, wild type Mo-MuLV; 3, negative control, pGCcos3neo. Protein molecular size markers (in kilodaltons) are indicated. (B) Hybridization of viral RNA. Virus samples were harvested and adjusted for equal amounts of p30$^{gag}$. RNA was isolated from virus pellets and hybridized to a Mo-MuLV gag-pol probe (extending from Xho I [nucleotide 1560 (T. Shinnick et al. (1981) *Nature* (London) 293, 543–548)] to Sal I [nucleotide 3705]). Lanes: 1, negative control, pGCcos3neo; 2, mutant C26S; 3, mutant C26S/C29S; 4, mutant C29S; 5, mutant Y28S; 6, mutant W35S; 7, mutant C39S; 8 and 9, 1:100 and 1:10 dilution of wild type Mo-MuLV, respectively; 10, wild type Mo-MuLV. RNA molecular size markers (in kilobases) are indicated.

According to the present invention, the infectivity of any retrovirus that contains at least one copy of the following amino acid sequence:

-Cys-X-X-Cys-X-X-X-X-His-X-X-X-X-Cys- (hereinafter referred to as the cysteine array) can be drastically reduced or completely eliminated by generating mutants that lack some or all of the invariant residues which constitute part of a vital protein structure common to all retroviruses and involved in the selection and packaging of genomic viral RNA into infectious virus particles.

In one embodiment, the mutation is such that the infectivity of the retrovirus is reduced by at least 3 orders of magnitude as measured by an infectivity assay. In another embodiment, the mutation is such that the infectivity of the retrovirus is reduced by at least 5 orders of magnitude as measured by an infectivity assay. In still another embodiment, the mutation is such that the retrovirus is rendered non-infective as measured by an infectivity assay.

The mutation may be an invariant residue of the amino acid sequence. Alternatively, the mutation may be a variant residue of the sequence.

The retrovirus may be human immunodeficiency virus (HIV), for example, human immunodeficiency virus 1 (HIV-1).

At least one mutation may be present in two of the cysteine arrays. The cysteine at positions 1 and 4 of the array may be replaced. The cysteine at position 1 of the array may be replaced. At least one mutation may be a deletion mutation.

In another embodiment of the invention, there is provided a vaccine effective against a retrovirus, comprising an altered form of the retrovirus having a mutation in a cysteine array present in the nucleocapsid domain of the gag precursor polyprotein of the virus, the cysteine array having the sequence -Cys-X-X-Cys-X-X-X-X-His-X-X-X-X-Cyswherein X represents variable amino acids.

Examples of the vaccine include a vaccine effective against human immunodeficiency virus (HIV), for example, human immunodeficiency virus 1 (HIV-1).

In still another embodiment of the invention, there is provided a therapeutic agent effective against a retrovirus, comprising (1) a therapeutically effective amount of an altered form of the retrovirus having a mutation in a cysteine array present in the nucleocapsid domain of the gag precursor polyprotein of the virus, the cysteine array having the sequence -Cys-X-X-Cys-X-X-X-X-His-X-X-X-X-Cyswherein X represents variable amino acids, and (2) a pharmaceutical carrier.

Examples of the therapeutic agent include a therapeutic agent effective against human immunodeficiency virus (HIV), for example, human immunodeficiency virus 1 (HIV-1).

As noted above, the present invention is directed to non-infectious human retroviruses, for example, human immunodeficiency virus (HIV). This virus contains two highly conserved cysteine arrays. As described in Example 2 below, mutations have been made in both cysteine arrays of HIV-1 and the results indicate that alteration of either cysteine array results in non-infectious or very poorly infectious particles.

Examples of specific retroviruses for which the sequence data of the arrays are available may be seen in Table 1 below.

TABLE 1

| virus | amino acid sequence containing arrays[a] |
|---|---|
| FeLV | CAY<u>C</u>KEKGHWAKD<u>C</u> |
| R-MuLV | CAY<u>C</u>KEKGHWAKD<u>C</u> |
| M-MuLV | CAY<u>C</u>KEKGHWAKD<u>C</u> |
| Akv-MuLV | CAY<u>C</u>KEKGHWAKD<u>C</u> |
| BaEV | CAY<u>C</u>KERGHWTKD<u>C</u> |
| SRV-1 | CFK<u>C</u>GRKGHFAKN<u>C</u>-($X_{15}$)-<u>C</u>PR<u>C</u>KRGKHWANE<u>C</u> |
| MMTV | CFS<u>C</u>GKTG<u>H</u>IKRD<u>C</u>-($X_{13}$)-<u>C</u>PR<u>C</u>KKGY<u>H</u>WKSE<u>C</u> |
| RSV | CYT<u>C</u>GSPG<u>H</u>YQAQ<u>C</u>-($X_{12}$)-<u>C</u>EL<u>C</u>NGMG<u>H</u>NAKQ<u>C</u> |
| BLV | CYR<u>C</u>LKEG<u>H</u>WARD<u>C</u>-($X_{11}$)-<u>C</u>PI<u>C</u>KDPS<u>H</u>WKRD<u>C</u> |
| HTLV-1 | CFR<u>C</u>GKAG<u>H</u>WSRD<u>C</u>-($X_9$)-<u>C</u>PL<u>C</u>QDPT<u>H</u>WKRD<u>C</u> |
| HIV-HXB2 | CFN<u>C</u>GKEG<u>H</u>TARN<u>C</u>-($X_7$)-<u>C</u>WK<u>C</u>GKEG<u>H</u>QMKD<u>C</u> |
| HIV-BH102 | CFN<u>C</u>GKEG<u>H</u>TARN<u>C</u>-($X_7$)-<u>C</u>WK<u>C</u>GKEG<u>H</u>QMKD<u>C</u> |
| HIV-PV22 | CFN<u>C</u>GKEG<u>H</u>TARN<u>C</u>-($X_7$)-<u>C</u>WK<u>C</u>GKEG<u>H</u>QMKD<u>C</u> |
| HIV-BH5 | CFN<u>C</u>GKG<u>H</u>IARN<u>C</u>-($X_7$)-<u>C</u>WK<u>C</u>GKEG<u>H</u>QMKD<u>C</u> |
| HIV-BRU | CFN<u>C</u>GKEG<u>H</u>IARN<u>C</u>-($X_7$)-<u>C</u>WK<u>C</u>GKEG<u>H</u>QMKD<u>C</u> |
| HIV-MN | CFN<u>C</u>GKEG<u>H</u>IAKN<u>C</u>-($X_7$)-<u>C</u>WK<u>C</u>GKEG<u>H</u>QMKD<u>C</u> |
| HIV-SF2 | CFN<u>C</u>GKEG<u>H</u>IAKN<u>C</u>-($X_7$)-<u>C</u>WR<u>C</u>GREG<u>H</u>QMKD<u>C</u> |
| HIV-CDC41 | CFN<u>C</u>GKEG<u>H</u>IARN<u>C</u>-($X_7$)-<u>C</u>WK<u>C</u>GREG<u>H</u>QMKD<u>C</u> |
| HIV-RF | CFN<u>C</u>GKVG<u>H</u>IAKN<u>C</u>-($X_7$)-<u>C</u>WK<u>C</u>GKEG<u>H</u>QMKD<u>C</u> |
| HIV-MAL | CFN<u>C</u>GKEG<u>H</u>LARN<u>C</u>-($X_7$)-<u>C</u>WK<u>C</u>GKEG<u>H</u>QMKD<u>C</u> |
| HIV-ELI | CFN<u>C</u>GKEG<u>H</u>IAKN<u>C</u>-($X_7$)-<u>C</u>WR<u>C</u>GKEG<u>H</u>QLKD<u>C</u> |
| HIV-2ROD | CWN<u>C</u>GKEG<u>H</u>SARQ<u>C</u>-($X_7$)-<u>C</u>WK<u>C</u>GKP<u>GH</u>IMTN<u>C</u> |
| HIV-2NIHZ | CWN<u>C</u>GKEG<u>H</u>SARQW-($X_7$)-<u>C</u>WK<u>C</u>GKSG<u>H</u>VMAN<u>C</u> |
| SIV-MM142 | CWN<u>C</u>GKEG<u>H</u>SARQ<u>C</u>-($X_7$)-<u>C</u>WK<u>C</u>GKMD<u>H</u>VMAK<u>C</u> |
| SIV-K6W78 | CWN<u>C</u>GKEG<u>H</u>SARQ<u>C</u>-($X_7$)-<u>C</u>WK<u>C</u>GKMD<u>H</u>VMAK<u>C</u> |
| EIAV | CYN<u>C</u>GKPG<u>H</u>LSSQ<u>C</u>-($X_5$)-<u>C</u>FK<u>C</u>KQPG<u>H</u>FSKQ<u>C</u> |
| VISNA | CYN<u>C</u>GKPG<u>H</u>LARQ<u>C</u>-($X_5$)-<u>C</u>HH<u>C</u>GKRG<u>H</u>MQKD<u>C</u> |

[a]Underlined residues are invariant.

The invariant nature of the cysteine array was first described in 1981 (L. Henderson et al. (1981) *J. Biol. Chem.* 256, 8400–8406); however, previous to now, its vital importance to vital replication has not been known.

Methods for constructing non-infectious retroviruses having substitutions, additions or deletions of invariant and variable residues within the cysteine array include, for example, oligonucleotide-directed mutagenesis (M. Zoller et al. (1982) *Nucl. Acids Res.* 10, 6487–6500) as described in Example 1 below. In addition, other methods whereby mutants can be constructed include cassette mutagenesis (J. Wells et al. (1985) *Gene* 34, 315–323), and sodium bisulfite mutagenesis (R. Pine et al. (1987) *Methods Enzymol.* 154, 415–430) of single stranded DNA regions prepared by the gapped duplex method (W. Kramer et al. (1987) *Methods Enzymol.* 154, 350–367), and polymerase chain reaction (A. Hemsley et al. (1989) *Nucl. Acids Res.* 17, 6545–6551).

The non-infectious retroviruses of the present invention can be used in the preparation of vaccines. As noted above, the infectivity of the mutants is drastically reduced or completely eliminated, as the mutants do not contain the normal complement of viral RNA; however, the surface components of the mutants are identical to the surface components of live virus containing viral RNA. Accordingly, antibodies can be raised against the surface components of the mutants and the antibodies thus generated will be effective against the live virus having corresponding surface features. Thus, the non-infectious retroviruses can be used in the design of vaccines which are safe to use and effective against any retrovirus.

With respect to HIV-1 mutants, it is believed that there are epitopes contained in the mutant virions (other than those from gp120) that have not previously been seen in other studies with viral protein subunit, peptide, heat or chemically inactivated virion inoculations. These are expected to elicit strong antibody responses and be less variable than the env epitopes that are currently under study. Thus, a wider range of HIV-1 strains are expected to be susceptible to immunization against these common epitopes.

To decrease the likelihood of infectious revertants, additional alterations can be introduced into a retroviral genome that will yield non-infectious particles and these particles will still remain essentially native-like in structure. These include the following: removal of the packaging or psi region of the genome, located in the 5' portion of the genome, prevents recognition and packaging of genomic RNA; alteration of the proviral 3' U3 region creates virions that, even if they do contain small amounts of RNA, could not initiate transcription upon subseqent infection cycles; removal of the gene coding for the integrase (IN) protein prevents subsequent integration of proviral sequences into the host cellular genome; and engineering multiple alterations into the clone decrease the chances of reversion.

The non-infectious retroviruses of the present invention can also be used in the development of effective diagnostic procedures for all known retroviruses, as well as the development of effective therapeutic agents. As indicated above, the present invention has enabled the determination of the biological role of the cysteine array, which has been found to be involved in the selection and packaging of genomic viral RNA into infectious virus particles. Because the structural features of all known retroviruses differ from each other except for this component, which is common to all, any method which detects the cysteine array or intervenes with its functioning can be used to detect all known retroviruses. Thus, for example, the cysteine array presents a target for devising reagents which can be used in the development of effective diagnostic procedures, as well as the development of therapeutic agents.

For example, the development of mutant HIV viruses that can, for only one round, normally infect and integrate into host genomic DNA is expected to be of great utility in AIDS studies and in large scale production of virions for reagent purposes. This procedure can, of course, be adapted to any intact retroviral clone. Since, for example, the mutant HIV-1 virions do not package their genomic RNA due to the inability of the nucleocapsid protein domain to recognize its genome, sequential transfection of a cysteine array mutant clone and a clone with an SV-40 (or other suitable) promoter linked to gag or gag-pol genes will allow for complementation of mutant virus proteins, resulting in the packaging of the mutant retroviral genome. The complementing SV-40/gag genome will not be packaged as there is no packaging signal. The resulting virus, with normal gag proteins and mutant genomic RNA, will be able to undergo one round of infection and integrate its provirus into susceptible cells, such as peripheral blood leukocytes (PBLs) or established cell lines. These cells will then have a stably integrated mutant genome that produces mutant virions. These mutant virions being expressed from this stable integation are once again unable to package their RNA genome since the only nucleocapsid proteins being produced in these cells are altered in the sensitive cysteine array region.

In another embodiment, mutant viral strains that are infectious for only one cycle are introduced into PBLs isolated from a patient and subsequently returned back into the patient blood stream. The infected PBLs will then express defective virus that will act as a constant source of immunogen. Over a period of time, the PBLs will die out and the mutant virions, since they are non-infectious, will be cleared from the patient.

In still another embodiment, H-9 or other suitable cells containing a stably integrated mutant provirus are obtained in a similar fashion. Such cells are then a continous source of mutant, non-infectious virus particles, resulting in increased safety in the laboratory or in diagnostic tests.

In yet another embodiment, the mutant viruses are utilized for the purposes of reagents in basic retroviral research. The viruses have the added safety of being non-infectious, yet they appear to be normal in all respects except for the absence of genomic RNA. The mutant viruses can be used as reagents for detecting antibodies in infected individuals as is now the case with kits using retroviral env component proteins or peptides. It is expected that there are other, less variable, epitopes present on these virions that will allow for the detection of a wider variety of viral strains.

In still another embodiment, the mutant viruses are used in the development of anti-retroviral agents. Due to the exquisite sensitivity of the conserved amino acid region to alteration, the development of chemical reagents targeted toward the amino acid sequence is expected to be of great utility in combating a retroviral infection. It will also prevent the further spread of retroviruses if used prophylactically. These reagents will bind to this region of the protein and render it useless in recognizing its genomic RNA, thus creating non-infectious virus.

Additionally, due to the highly conserved nature of these arrays found in all retroviral nucleocapsid proteins, screening procedures to detect any and all retroviruses can be developed. These screening procedures will be useful in identifying retroviruses that have been implicated in a number of diseases. The screening procedures may include detection of common nucleotide sequences found in the gag gene coding for this conserved cysteine array or the detection of the nucleocapsid proteins containing this common region.

The present invention will be illustrated in detail in the following Examples. These Examples are included for illus- Plasmids: All viral subclones were derived from an infectious clone of Moloney murine leukemia virus (M-MuLV) originally obtained from D. Steffen (A. Rein et al. (1986) *Proc. Natl. Acad. Sci. USA* 83, 7246–7250). A complete infectious clone (designated pRR88) containing the M-MuLV genome in a selectable vector was constructed using 14.0-kilobase (Kb) Eco RI-Xho I fragment from a clone of M-MuLV in Charon 4A vector, and the 6.5 kb Eco RI-Sal I portion of the pGCcos3neo selectable vector (a gift from Gray Crouse, Emory University, Atlanta, Ga.) which is a modified version of the pSV2neo vector containing a Sal I site (P. Southern et al. (1982) *J. Mol. Appl. Genet.* 1, 5177–5181); pUC118 (J. Vieira et al. (1987) *Meth. Enzym.* 153, 3–11) was a gift of J. Vieira (Rutgers Campus, State University of New Jersey, New Brunswick, N.J.). A c-Ki-ras clone, pSW11.1 (M. McCoy et al. (1984) *Mol. Cell. Biol.* 4, 1577–1582), was a gift of M. Barbacid (National Cancer institute-Frederick Cancer Research Facility).

Cloning and Mutagenesis Reagents: All cloning enzymes used in this work were from either New England Biolabs, or Bethesda Research Laboratories. All plasmid preparations used were cesium banded. Mutagenic oligonucleotides and the Pst I-Xho I adaptor (see below) were prepared on an Applied Biosystems 380B DNA Synthesizer. The sequences of the mutagenic oligonucleotides are listed in Table 2 below:

TABLE 2

| Oligo | Size | Starting Position* | Sequence (5'->3') |
|---|---|---|---|
| C26S | 20 | 2117 | CGA TCG CGA CCA GTC TGC CT |
| C26S/C29S | 27 | 2117 | CGA TCG CGA CCA GTC TGC CTA CTC CAA |
| C29S | 20 | 2126 | CCA GTG TGC CTA CTC CAA AG |
| Y28S | 20 | 2123 | CGA CCA GTG TGC CTC CTG CA |
| W35S | 20 | 2144 | AGA AAA GGG GCA CTC GGC TA |
| C39S | 20 | 2156 | CTG GGC TAA AGA TTC TCC CA |

*Nucleotide position of M-MuLV sequence (T. Shinnick et al. (1981) *Nature* (London) 293, 543–548)

trative purposes and should not be considered to limit the present invention.

EXAMPLE 1

Generation of Mutations in Moloney Murine Leukemia Virus Nucleocapsid Protein, p10$^{gag}$ Methodology:

Cell Lines: Chinese hamster ovary (CHO) cells were described previously (M. Gottesman, ed. (1985) *Molecular Cell Genetics* (Wylie-Interscience, New York), p. 883; A. Rein et al. (1986) *Proc. Natl. Acad. Sci. USA* 83, 7246–7250). The K-NRK line of rat cells transformed by Kirsten sarcoma virus (KiSV) (S. Aaronson et al. (1971) *J. Gen. Virol.* 13, 245–252) was a gift of Steve Showalter (National Cancer Institute-Frederick Cancer Research Facility).

Bacteria: Library efficiency DH5α competent cells used for transformations involving non-M13 plasmids and DH5αF' competent cells used for transformations with M13 type plasmid constructs were obtained from Bethesda Research Laboratories. Transformation of these hosts with plasmid constructs were performed according to the manufacturers protocols.

Mutagenesis: Mutagenesis was performed in a pUC118 subclone of Moloney MuLV (designated pRR89) which extended from the Xho I site (nucleotide 1560 [T. Shinnick et al. (1981) *Nature* (London) 293, 543–548]) to the Sal I site (nucleotide 3705), using an oligonucleotide as a single-stranded adaptor or "bandaid" between the Moloney Xho I site and the pUC118 Pst I site. The adaptor was 5' phosphorylated (M. Zoller et al. (1982) *Nucl. Acids Res.* 10, 6487–6500) and had the following sequence: 5'-TGAGGCTGCA-3'. The ligation was performed with a 500-fold molar excess of the adaptor over the vector and the 2145 bp insert (ligation consisted of 0.1 pmole of 2145 bp insert and 0.01 pmole of pUC118 vector). Single-stranded DNA was obtained by superinfecting TG1 bacteria containing the Moloney subclone with M13K07 (a gift of J. Vieira) as described (J. Vieira et al. (1987) *Meth. Enzym.* 153, 3–11). Other plasmid vectors from which one can recover single stranded DNA for mutagenesis templates include the M13mp series, pUC100 series, or Bluescript vectors. Oligonucleotide-directed mutagenesis was performed using reagents and procedures supplied by Amersham Corp. (Arlington Heights, Ill.). In each case, candidate mutant plasmids were analyzed by chain termination sequencing of single-stranded DNA (F. Sanger et al. (1977) *Proc. Natl.*

*Acad. Sci. USA* 74, 5463–5467) using Sequenase (U.S. Biochemical Corp., Cleveland, Ohio) between the Xho I site and the Sac I site at nucleotide 2554. Templates for sequencing were constructed by insertion of mutant 1003 bp Pst I-Sal I fragments into homologous restriction sites of M13mp18. Oligonucleotides for verifying the mutant 994 bp Xho I-Sac I sequences were prepared as described above and are listed in Table 3 below:

TABLE 3

| Oligo | Size | Starting Position* | Sequence (5'->3') |
|---|---|---|---|
| A | 26 | 2576 | AAC CCT CAA AGT CGG GGG GCA ACC CG |
| B | 26 | 2366 | TGA TAA GTC TGC CTG GGT CCA AGG GG |
| C | 26 | 2456 | CAC CCA CTC TTT CCT CCA TGT ACC AG |
| D | 26 | 2186 | AGG ACC TCG GGG ACC AAG ACC CCA GA |
| E | 21 | 3656 | TGC CCC AGC CCT GGG GTT GCC |
| F | 21 | 3356 | GGC CTC GGC CAA GAA AGC CCA |
| G | 21 | 2756 | AGC AAC CTC TAC CCC CGT GTC |
| H | 21 | 3056 | TGC CTT TTT CTG CCT GAG ACT |

*Nucleotide position of M-MuLV sequence (T. Shinnick et al (1981) *Nature* (London) 293, 543–548)

This 994 BP Xho I-Sac I fragment, containing the wild-type sequence except for the desired change, was then used in the reconstruction of the intact M-MuLV genome. Mutant virus constructions were performed by ligating the mutant 994 BP Xho I-Sac I fragment made from pRR89 (see above) with the 5.1 kb Sac I-Cla I and the 13 kb Xho I-Cla I portions from the infectious clone (pRR88). To ensure that the reconstructed mutant plasmids contained no defects other than the desired mutation, the 994 BP Xho I-Sac I mutant fragment in each case was replaced with the corresponding fragment from wild-type pRR89. The resulting plasmids (constructed as described above) gave rise to fully infectious M-MuLV upon transfection into hamster cells, based upon transient infectivity assays. Mutations are designated as follows: a mutation changing the cysteine codon at position 26 of p10$^{gag}$ to a serine codon is named C26S.

Transfection and Tissue Culture Maintenance: Viral DNA constructs were introduced into Chinese hamster ovary (CHO) and the K-NRK line of rat cells transformed with Kirsten sarcoma virus by calcium phosphate coprecipitation (F. Graham et al. (1973) *Virology* 52, 456–467) and 48 h after transfection, cells containing the viral constructs and thus neomycin resistance were selected using 400 µg/ml G418 (Geneticin, Bethesda Research Laboratories). CHO cells were grown in alpha modified Eagle medium in the presence of 5% fetal calf serum, 400 µg/ml G418 and 0.3 µM dexamethasone in an atmosphere supplemented with 5% $CO_2$ at 37° C. K-NRK cells were carried in Dulbeccos modified Eagle medium with 10% fetal calf serum under identical conditions.

Virus Assays: Infectivity and reverse transcriptase assays were as described (R. Bassin et al. (1971) *Nature* (London) 229, 564–566; A. Rein et al. (1979) *J. Virol.* 29, 494–500; A. Rein (1982) *Virology* 120, 251–257; B. Gerwin et al. (1979) *J. Virol.* 31, 741–751). All infectivity assays except for S$^+$L$^-$ focus assay were performed in NIH/3T3 cells. In all experiments in which virus was harvested, the cells were treated with $3 \times 10^{-7}$M dexamethasone (Sigma, St. Louis, Mo.) for several days before harvest.

Isolation of Virus and Viral RNA: Cultures of cells transfected with mutant and wild type viral constructs were grown to approximately 80% confluency in 150 cm² flasks. Cells were fluid changed with 35 ml of their respective media (see above) and incubated overnight. Virus was harvested by centrifugation through a 4 ml cushion of 20% sucrose in diethylpyrocarbonate-treated phosphate buffered saline (R. Dulbecco et al. (1954) *J. Exp. Med.* 99, 167–182) at 25,000 RPM for 2.5 hr in a Beckman SW-27 rotor at 4° C.

Protein Immunoblotting and Immunoprecipitations: Viral proteins were fractionated by NaDodSO$_4$-PAGE using 10–20% acrylamide gradient gels and transferred to diazotized paper as described (J. Symington et al. (1981) *Proc. Natl. Acad. Sci. USA* 78, 177–181). Goat antiserum to p30$^{gag}$ (R. Versteegen et al. (1980) *J. Virol.* 33, 983–992) was used and the antigen-antibody complex was visualized with $^{125}$I-Protein G (Amersham Corp.). Immunoprecipitations using Protein A Sepharose (Pharmacia) were performed according to previous procedures (A. Schultz et al. (1983) *J. Virol.* 46, 355–361; A. Schultz et al. (1979) *J. Virol.* 30, 255–266). Antisera to the major gag protein (p30$^{gag}$) and to the env protein gp70 were supplied by Dr. Alan M. Schultz (Laboratory of Molecular Virology and Carcinogenesis, NCI-Frederick Cancer Research Facility, Frederick, Md.). Densitometric analysis of autoradiograms was performed using a Biomed Instruments Soft Laser Scanning Densitometer model SL504.

Nucleic Acid Hybridization: RNA was isolated from virus particles as described (M. Bender et al. (1987) *J. Virol.* 61, 1639–1646). Viral RNAs were separated on denaturing agarose gels (T. Maniatis et al. (1982) *Molecular Cloning A Laboratory Manual* (Cold Spring Harbor Laboratory, Cold Spring Harbor, N.Y.), transferred to nitrocellulose, and hybridized with $^{32}$P-labeled nick-translated probes as described (T. Maniatis et al. (1982) *Molecular Cloning A Laboratory Manual* (Cold Spring Harbor Laboratory, Cold Spring Harbor, N.Y.; P. Thomas (1980) *Proc. Natl. Acad. Sci. USA* 77, 5201–5205). Hybridized filters were washed three times in 2× SSC, 0.01% NaDodSO$_4$, at 42° C. for 5 min, two times in 1× SSC, 0.01% NaDodSO$_4$ at 54° C. for 20 min, and two times in 0.5× SSC at 54° C. for 5 min (1× SSC is 0.15M NaCl, 0.015M sodium citrate).

Results:

As described above, site-directed mutagenesis was performed, creating five point mutations individually changing each of the underlined amino acids to serine as follows:

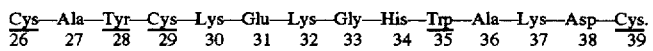

Cys—Ala—Tyr—Cys—Lys—Glu—Lys—Gly—His—Trp—Ala—Lys—Asp—Cys.
 26   27   28   29   30   31   32   33   34   35   36   37   38   39

In addition, one double mutant encoding serine at both position 26 and position 29 was generated.

Intact Moloney MuLV genomes containing these mutations were placed in the selectable vector pGCcos3neo. The mutants were initially transfected into both hamster and mouse cells. However, the mutants frequently reverted to wild type in mouse cells, presumably by recombination with endogenous MuLV sequences (J. Colicelli et al. (1987) *Virology* 160, 518–522). Due to this problem, the experiments described in this example were performed in hamster cells.

Mass cultures of neo cells were tested for virus particle production by several types of assays. As is shown in Table 4 below, culture fluids were found to contain particle-associated reverse transcriptase activity at essentially the same level as the control culture transfected with the wild-type parental plasmid.

TABLE 4

Properties of p10$^{gag}$ mutants

| Virus | p30* | RT† | Infectivity | |
|---|---|---|---|---|
| | | | FIU/ml‡ | CPFU/ml§ |
| C26S | 27 | 59 | <1 × 10⁰ | <1 × 10⁰ |
| C29S | 23 | 52 | <1 × 10⁰ | <1 × 10⁰ |
| C26S/C29S | 26 | 32 | <1 × 10⁰ | <1 × 10⁰ |
| Y28S | 38 | 86 | <1 × 10⁰ | 9 × 10² |
| W35S | 19 | 23 | <1 × 10⁰ | 2 × 10⁰ |
| C39S | 29 | 63 | <1 × 10⁰ | 3 × 10⁰ |
| Wild type | 27 | 69 | 7 × 10⁵ | N.D.** |

CHO cells were transfected with plasmids containing mutant or wild type MuLV genomes, and stable transfectants were selected with G-418. Culture fluids from these cultures were assayed as indicated. Mutants are designated as follows: C26S is a mutant in which the cysteine codon at position 26 of p10$^{gag}$ is changed to a serine codon.
*p30, protein immunoblotting results (see FIG. 1A) expressed in arbitrary densitometric units.
†RT, reverse transcriptase activity, pmol of [³H]TMP incorporated per ml of culture fluid (B. Gerwin et al. (1979) *J. Virol.* 31, 741–751).
‡FIU/ml, focus-inducing units/ml in the S⁺L⁻ focus assay (R. Bassin et al. (1971) *Nature* (London) 229, 564–566).
§CPFU/ml, complementation plaque-forming units/ml (A. Rein et al. (1979) *J. Virol.* 29, 494–500).
**N.D., not determined.

However, the culture fluids were negative in the UV-XC test and the S⁺L⁻ focus assay, which both measure the concentration of MuLV particles capable of efficient replication in mouse cells. They were also tested in the complementation plaque assay. In this test, a complementing "helper" virus is added to the assay plate; any particles capable of initiating even a single round of infection in mouse cells will register in this assay (A. Rein et al. (1979) *J. Virol.* 29, 494–500). All of the mutants except Y28S were at least five orders of magnitude less efficient than wild type in introducing the M-MuLV genome into target cells (CPFU value) as determined in this test. The single point mutation in the Y28S mutant also produce virus incapable of continuous rounds of infection and replication (FIU value), however, this virus was capable of infecting cells with an efficiency about three orders of magnitude less than that of the wild type virus in the CPFU assay. Thus, the mutations allow the production of virus particles containing active reverse transcriptase, but these virions are totally noninfectious in the case of five of the mutants and only poorly infectious in the case of Y28S. These results strongly support the hypothesis that the amino acids in the finger-like sequence are crucial for virus replication.

The particles were also examined by protein immunoblotting, using antiserum against the major core protein p30$^{gag}$. FIG. 1A shows the results obtained with mutant C39S (lane 1) as well as with positive and negative controls. As can be seen, C39S particles give profiles identical to that of the wild type control. Essentially identical results were obtained with all of the mutants. These results confirm that the mutations do not impair virus particle production. Further, they show that the viral protease is functioning normally in the mutants, cleaving the gag polyprotein precursor to the mature gag proteins. In other tests of the cultures containing the mutant MuLVs, normal-looking budding particles were seen by electron microscopy of thin sections, and normal levels of env proteins were detected by radioimmunoprecipitation.

Figure 1B:
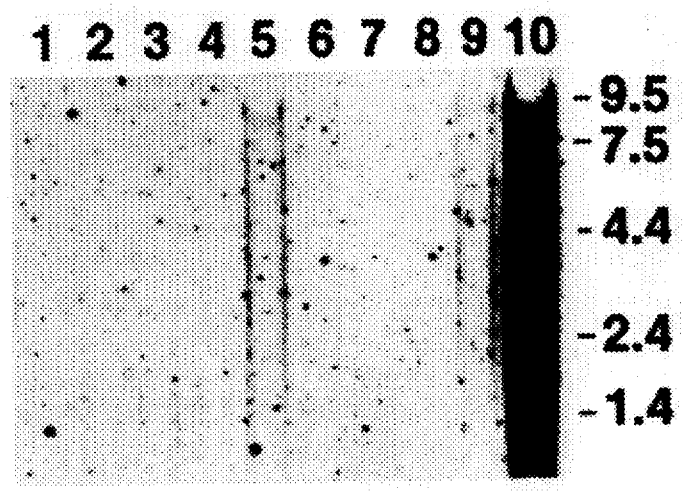

The virus particles were also tested for the presence of viral RNA. RNA was isolated from the particles and was tested by hybridization for the presence of viral sequences. Equal quantities of virus (as assayed by protein immunoblotting for p30$^{gag}$) were loaded onto each lane. As shown in FIG. 1B, none of the mutants except Y28S contained detectable viral RNA. Lanes 9 and 8 contain successive 10-fold dilutions of the wild-type control RNA; this calibration indicates that Y28S particles contain approximately ¹⁄₁₀ as much viral RNA as wild type, while the other mutants contain less than ¹⁄₅₀ of the wild-type level. These results show that the mutations prevent encapsidation of the viral RNA.

Figure 2:
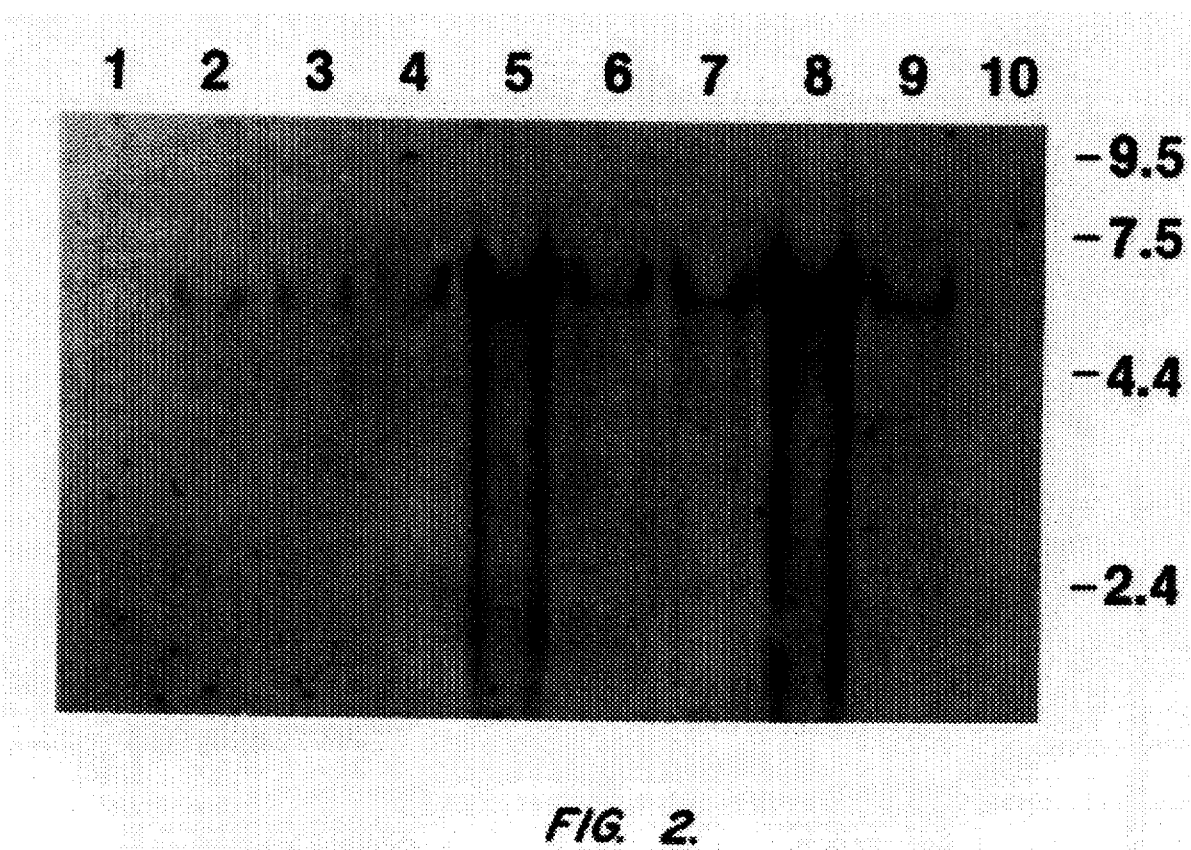
FIG. 2. Hybridization of RNA from virus contained in culture fluids from KiSV transformed rat cells. K-NRK cells were transfected with plasmids containing mutant or wild type Mo-MuLV genomes, and stable transfectants were selected with G-418. Virus samples were harvested and adjusted for equal amounts of p30$^{gag}$. RNA was isolated from virus pellets and hybridized to a 1 kilobase Pst I-Sal I Kirsten-ras probe (M. McCoy et al. (1984) *Mol. Cell. Biol.* 4, 1577–1582). Lanes: 1, negative control, pGCcos3neo; 2, mutant C26S; 3, mutant C26S/C29S; 4, mutant C29S; 5, mutant Y28S; 6. mutant W35S; 7. mutant C39S; 8. wild type Mo-MuLV; 9 and 10, 1:10 and 1:100 dilution of wild type Mo-MuLV, respectively. RNA molecular size markers (in kilobases) are indicated.

The mutations described herein are in a protein-coding region of the MuLV genome. In principle, the failure of the mutant particles to package viral RNA could reflect either an alteration in the viral protein, rendering it unable to function in recognizing or packaging the viral RNA; or an alteration of "packaging" sequences in the RNA itself, making it unrecognizable by the viral proteins involved in encapsidation. Therefore, the ability of the mutants to package a second RNA, known to be packaged with high efficiency by wild-type M-MuLV proteins, was tested. Plasmids containing the mutant or wild-type MuLV genomes were transfected into the K-NRK rat cell line transformed by KiSV, and stable transfectants were isolated. The particles produced by these cultures were then analyzed for KiSV genomic RNA by hybridization. The rescue depends upon the ability of the viral gag precursor polyprotein to specifically recognize and complex with the Kirsten-ras genomic RNA. As shown in FIG. 2, the mutant particles all contain less KiSV RNA than the wild-type control; it was estimated from lanes 8 and 9 that the deficiency in KiSV RNA packaging ranges from ¹⁄₃₀ (mutants C26S and C26S/C29S) to ½ (mutant Y28S). These data demonstrate that the mutations in the p10$^{gag}$ coding region have impaired the ability of the viral proteins to package viral RNA.

It is useful to compare FIG. 2 with FIG. 1B; the mutants seem significantly more deficient in packaging MuLV RNA than KiSV RNA. This discrepancy is consistent between the different experiments, since results virtually identical to those shown in FIG. 1B were obtained when the blot shown in FIG. 2 was "stripped" by heating to 100° C. and then rehybridized with an MuLV-specific probe.

The fluids analyzed in FIG. 2 were also tested by infectivity assays for MuLV and KiSV. As shown in Table 5 below, low levels of infectious KiSV were "rescued" by the mutant MuLVs.

TABLE 5

Properties of KiSV stocks "rescued" by p10$^{gag}$ mutants.

| Virus | p30* | Infectivity | | KiSV specific infectivity§ |
|---|---|---|---|---|
| | | FFU/ml† | CPFU/ml‡ | |
| C26S | 14 | $2 \times 10^0$ | $<1 \times 10^0$ | .00009 |
| C29S | 17 | $4 \times 10^0$ | $<1 \times 10^0$ | .0001 |
| C26S/C29S | 33 | $2 \times 10^1$ | $1 \times 10^0$ | .0004 |
| Y28S | 37 | $2 \times 10^3$ | $3 \times 10^1$ | .03 |
| W35S | 60 | $5 \times 10^2$ | $1 \times 10^0$ | .005 |
| C39S | 25 | $4 \times 10^1$ | $<1 \times 10^0$ | .001 |
| Wild type | 44 | $7 \times 10^4$ | $4 \times 10^4$ | (1) |

K-NRK cells were transfected with plasmids containing the indicated viral genomes, and stable neo$^r$ transfectants were isolated. Culture fluids were assayed as indicated.
*p30, protein immunoblotting results expressed in arbitrary densitometric units.
†FFU/ml, focus-forming units of KiSV/ml. A. Rein (1982) Virology 120, 251–257
‡CPFU/ml, complementation plaque-forming units/ml.
§KiSV specific infectivity, FFU:p30 ratio of mutant/FFU:p30 ratio of wild type.

The KiSV titers were, however, much higher than the titers of MuLV particles able to infect the assay cells (i.e., CPFU). The ratio of mutant to wild type CPFU values is the same for the data given in Tables 4 and 5 showing the reproducibility of these results. Significantly, the specific infectivities of the KiSV rescued by the mutants (shown in the far right column of Table 5) were far lower than the KiSV RNA content of these particles (FIG. 2). The significance of these quantitative comparisons is discussed below.

Figure 3:
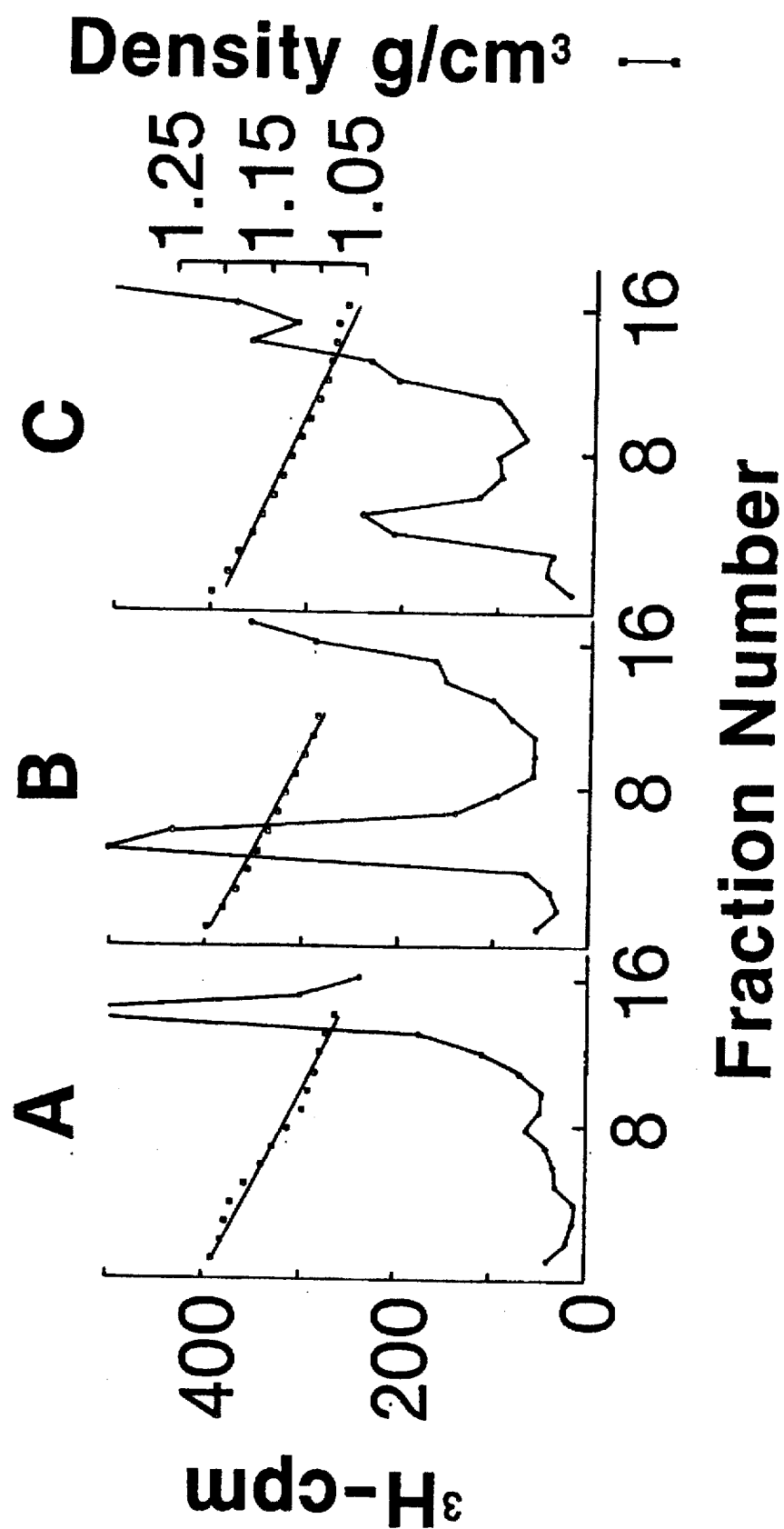
FIG. 3. $^3$H-uridine counts of sucrose banded mutants and wild type virus. Cells containing mutant or wild type viral constructs in 150 cm$^2$ flasks were labeled with 4 ml of media containing 0.1 mCi/ml[5-$^3$H]-uridine for 12 hours, and virus was harvested by centrifugation. For each sample, virus from three flasks was layered on a 10–50% sucrose gradient in 100 mM NaCl, 10 mM TRIS, pH 7.4, 1 mM EDTA. Gradients were centrifuged for 36 hr in a Beckman SW-41 rotor at 40,000 RPM, 4° C. ~1 ml fractions were removed from the bottom of each sample. (-□-) density of fraction in g/cm$^3$. (-o-) $^3$H-CPM of fraction. Panel A: negative control, pGCcos3neo. Panel B: wild type Mo-MuLV. Panel C: mutant C26S.

The foregoing results indicate that the mutant particles are deficient in their ability to package viral RNA. It was considered important to determine whether this deficiency reflected an inability to specifically recognize and package viral RNA, or a total loss of the capacity to incorporate RNA into virus particles. Therefore, the particles produced by the mutants were tested for the presence of RNA. Cultures producing mutant or wild-type virus were labeled for 12 hr with $^3$H-uridine. The particles produced by these labeled cultures were then banded in isopycnic sucrose gradients. Three representative gradients are shown in FIG. 3: a peak of radioactivity is present at 1.16 g/ml in fluids containing wild-type or C26S mutant MuLV, while no peak is observed in fluids from the control cells transfected with the plasmid vector alone. Essentially similar results were obtained with all of the mutants. In order to verify that the peak of radioactivity at 1.16 g/ml represents RNA within virus particles, its sensitivity to digestion with pancreatic ribonuclease was examined. As seen in Table 6 below, it was found that at least 50% of the radioactivity in the mutant viral peaks remained acid-precipitable after direct exposure to either 100 µg/ml RNase or 1% Triton X-100, but that they were rendered completely acid-soluble if they were treated with 1% Triton X-100 before RNase digestion.

TABLE 6

$^3$H-URIDINE LABELING OF VIRAL RNA

| | Untreated Control$^a$ | TRITON-X 100$^b$ | RNAse$^c$ | RNAse & TRITON-X 100 |
|---|---|---|---|---|
| C26S | 504 | 281 | 266 | 26 |
| C29S | 482 | 260 | 230 | 44 |
| C26S,C29S | 258 | 112 | 154 | 40 |
| Y28S | 394 | 188 | 183 | 34 |
| W35S | 178 | 108 | 102 | 50 |
| C39S | 334 | 172 | 216 | 47 |
| Wild Type | 687 | 390 | 367 | 71 |
| pGCcos3neo | 94 | 58 | 52 | 40 |

$^a$Table shows TCA-precipitable CPM remaining after the indicated treatments of sucrose-banded virus.
$^b$1% Triton-X 100.
$^c$100 µg/mL RNAse A.

These results indicate that the mutant particles do contain RNA; thus, the mutations in p10$^{gag}$ seem to have destroyed the specificity of the viral proteins for viral RNA, rather than the ability of the particles to take up RNA per se.

The point mutations obtained herein were all in an extremely highly conserved sequence which bears some resemblance to the metal-binding domains ("zinc fingers") found in a number of eukaryotic transcription factors. The present inventors found that each mutant gives rise to virus particles, but that these particles lack viral RNA. Since the particles do contain some RNA, the mutations have eliminated the specificity with which the viral proteins normally recognize and encapsidate the viral genome. Thus, the finger-like sequence motif in the p10$^{gag}$ appears to play an essential role in this recognition process.

The above-described experiments have shown that in the case of the example virus (M-MuLV), the cysteine residues in these structures are absolutely required for infectious and replicating virus, and the present inventors conclude that all retroviruses will have a similar requirement for these residues. Since the histidine residue is also invariant in the examples given in Table 1, it is concluded that this residue is also required for infectious replicating virus. It is concluded that each of these residues functions in an as yet unspecified manner to enable the gag precursor polyproteins to specifically complex with viral RNA, however, additional functions are not excluded.

The methods of site directed mutagenesis to incorporate specific site, deletion and addition mutations, have been used herein to study the function of the invariant residues in the array of the example virus. It is concluded that similar mutations altering residues in the invariant arrays of any retrovirus will generate mutant forms of that virus with properties similar to those of the example given herein. Thus, for any retrovirus, it will be possible to mutate invariant residues in the arrays and produce mutant forms of the virus that are normal in all respects but do not contain significant levels of genomic viral RNA and have drastically reduced or no infectivity. Such mutants are expected to have important applications as immunogens or as sources of mature vital proteins without accompanying biological hazard.

EXAMPLE 2

Generation of Mutations in the gag Gene Coding for the Nucleocapsid Protein of HIV-1

Mutations were made in the gag gene coding for the nucleocapsid protein of HIV-1 using the methods described in Example 1 above. These mutations, introduced by the technique of oligonucleotide directed mutagenesis, are shown in Table 7 below.

indicated that the viral protease was being expressed and was functioning properly. It is noted further that there were some uncleaved gag precursors detected by this antisera, in

TABLE 7

Mutations Made in the Nucleocapsid Protein of HIV-1

| WILD TYPE | NC ARRAY 1 | | | | | | | | | | | | | NC ARRAY 2 | | | | | | | | | | | |
|---|---|---|---|---|---|---|---|---|---|---|---|---|---|---|---|---|---|---|---|---|---|---|---|---|---|
| | C | F | N | C | G | K | E | G | H | I | A | K | N | C | C | W | K | C | G | K | E | G | H | Q | N | K | D | C |
| C15S/C18S[a] | S | — | — | S | — | — | — | — | — | — | — | — | — | — | — | — | — | — | — | — | — | — | — | — | — | — | — | — |
| C36S/C39S | — | — | — | — | — | — | — | — | — | — | — | — | — | — | S | — | — | S | — | — | — | — | — | — | — | — | — | — |
| Deletion-array 1 | I | .. | .. | .. | .. | .. | .. | .. | .. | .. | .. | .. | .. | .I | — | — | — | — | — | — | — | — | — | — | — | — | — | — |
| C36S | — | — | — | — | — | — | — | — | — | — | — | — | — | — | S | — | — | — | — | — | — | — | — | — | — | — | — | — |

[a]Numeral refers to the position of the amino acid residue in the mature HIV-1 NC protein The complete mutant HIV-1 clones were transfected into HeLa cells using CaPO$_4$ precipitates and virus was harvested three to five days after transfection. The resulting mutant viruses were characterized by various immunochemical, protein, nucleic acid, and infectivity methods.

Mutant viral supernatants were tested for the presence of p24, using the DuPont p24 antigen capture kit. Also, the presence of reverse transcriptase (RT) activity was examined by following the incorporation of $^3$H-TTP into oligo-dT-poly(A) primer-template complexes. These results are shown in Table 8 below.

TABLE 8

Properties of HIV-1 Mutants

| Mutant | p24$^{CA}$ Content[a] (ng/mL) | 'RT Activity[b] $^3$H-TTP incorporated (cpm) | Ratio[c] RT/p24$^{CA}$ |
|---|---|---|---|
| C15S/C18S | 20.9 | 19,700 | 942 |
| C36S/C39S | 10.1 | 8,800 | 871 |
| Array #1 deletion | 7.3 | 10,500 | 1,438 |
| C36S | 9.6 | 12,000 | 1,250 |
| Wild Type | 10.4 | 15,500 | 1,490 |

[a]The p24$^{CA}$ content of clarified supernatants from Hela cells transfected with mutant and wild type HIV-I clones was tested using the DuPont HIV p24 Core Antigen ELISA kit.
[b]Reverse transcriptase activity was determined by precipitating 0.5 mL of clarified culture fluid with 0.25 mL of 50% polyethylene glycol (8000 MW) in 0.5M NaCl. Precipitates were pelleted by centrifugation and dissolved in TNE buffer. Reverse transcriptase assays were performed on 1/5 of each sample as described (A. Hoffman et al. (1985) Virology 147, 326–335).
[c]Ratio of p24$^{CA}$ (ng/mL)/RT activity (cpm)

The amounts of virus produced was quite variable which is believed to reflect the inherent variabilities in the transfection procedure. An average of 12 ng of p24 CA protein was detected per mL of supernatant, five days after transfection, from a 24 hour harvest of 30 mL of supernatant from a confluent 150 cm$^2$ monolayer of HeLa cells. The p24 antigen capture results and RT activities showed reasonable agreement, indicating that the mutants had normal amounts of RT per virus particle.

Figure 4:
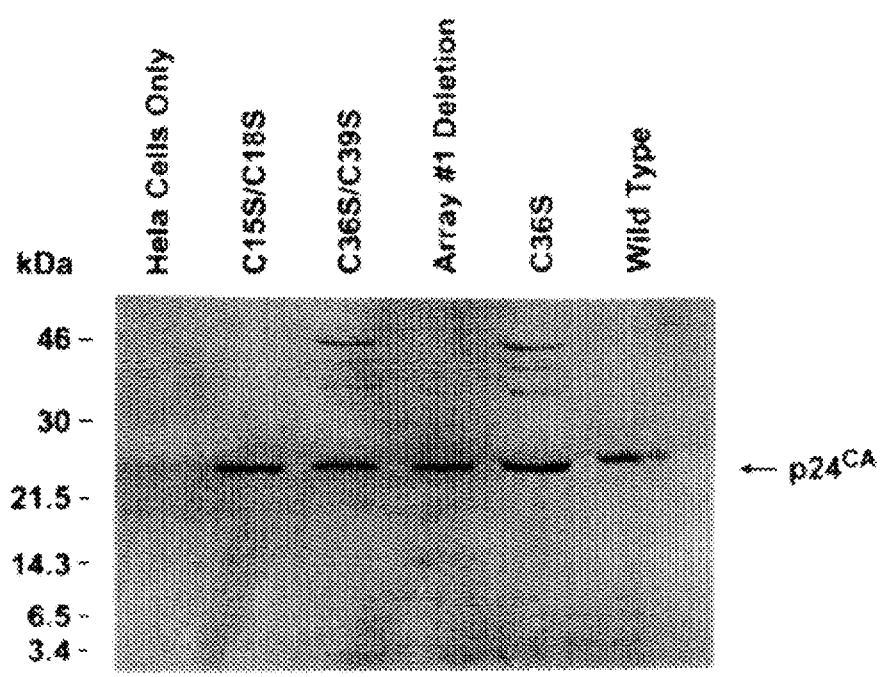
FIG. 4. Protein immunoblotting of mutant and wild type HIV-I using p24 CA monoclonal antibody. Hela cells were transfected with mutant and wild type viral clones. Four days later, clarified culture fluids were pelleted through a 1.0 mL cushion of 20% sucrose in phosphate buffered saline. Samples were adjusted for equal amounts of reverse transcriptase activities and processed for protein immunoblotting. The p24 CA monoclonal antibody complex was visualized using horseradish peroxidase staining. Samples are as labeled on the figure.

For all of the following experiments, each supernatant was adjusted for constant amounts of virus based on the reverse transcriptase data. Immunoblotting was performed and proteins were visualized by probing with monoclonal antibody to p24 (FIG. 4). It appeared that all of the mutant virions process their gag gene products identically to that of wild type virus, yielding mature CA protein (p24). This the wild type as well as in these mutants. Thus, it appeared that the mutant HIV-1 virions had functional gag and pol genes as seen from the Western assay shown in FIG. 4 and the reverse transcriptase (RT) data shown in Table 8.

Figure 5:
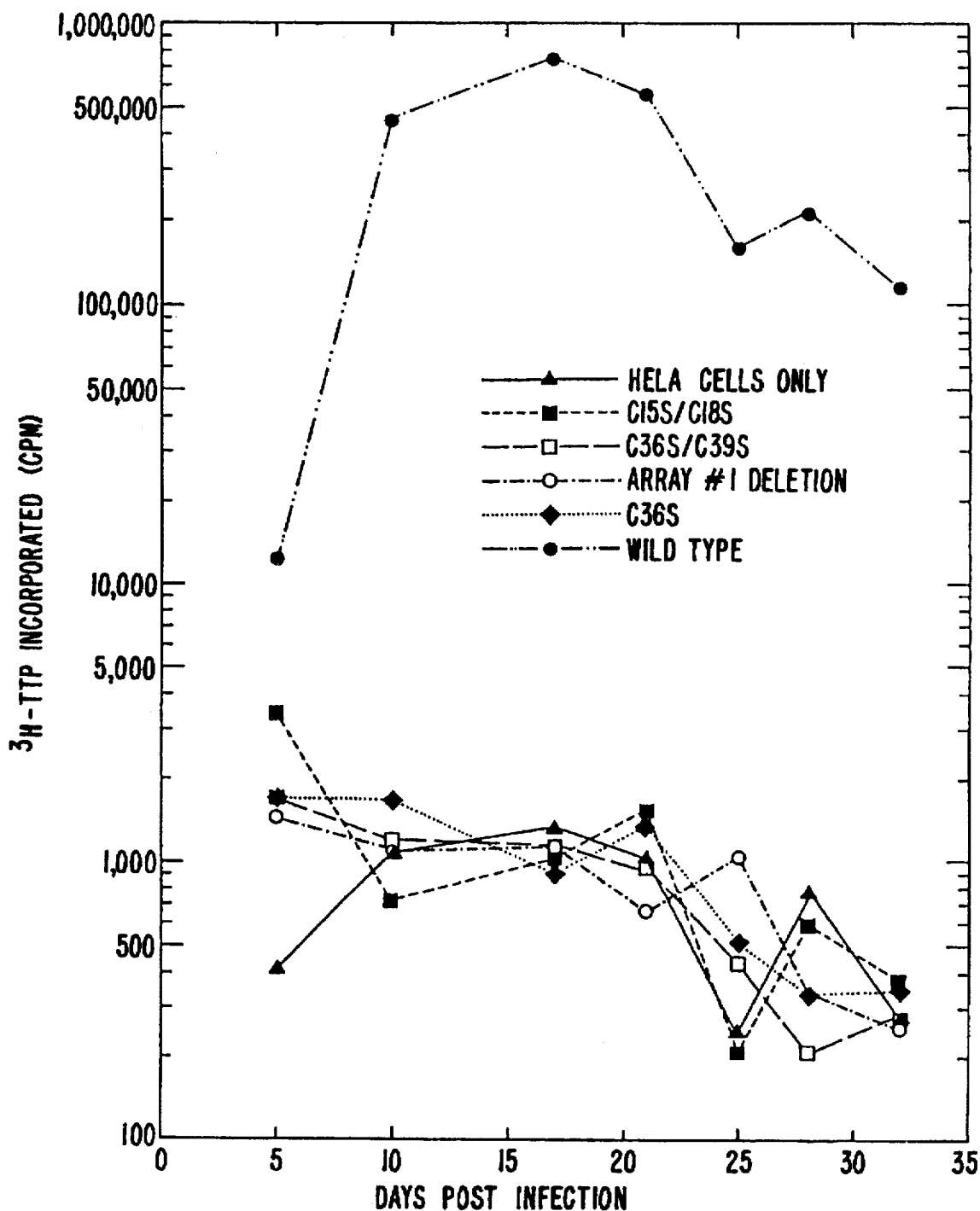
FIG. 5. Infectivity assay of supernatants from Hela cells transfected with wild type and mutant HIV-I clones. Clarified supernatants from the transfected Hela cells were adjusted for equal amounts of reverse transcriptase activity in an equal volume of inoculum. These supernatants were incubated with H9 cells for 12 h in the presence of 2 µg/mL polybrene. Nine mL of complete media containing 2 µg/mL polybrene was added to the incubations and the H9 suspensions were transferred to 25 cm$^2$ tissue culture flasks. On the days indicated, samples were removed from these H9 cultures, clarified and tested for the presence of reverse transcriptase activity. The samples tested are noted on the figure.
Figure 6:
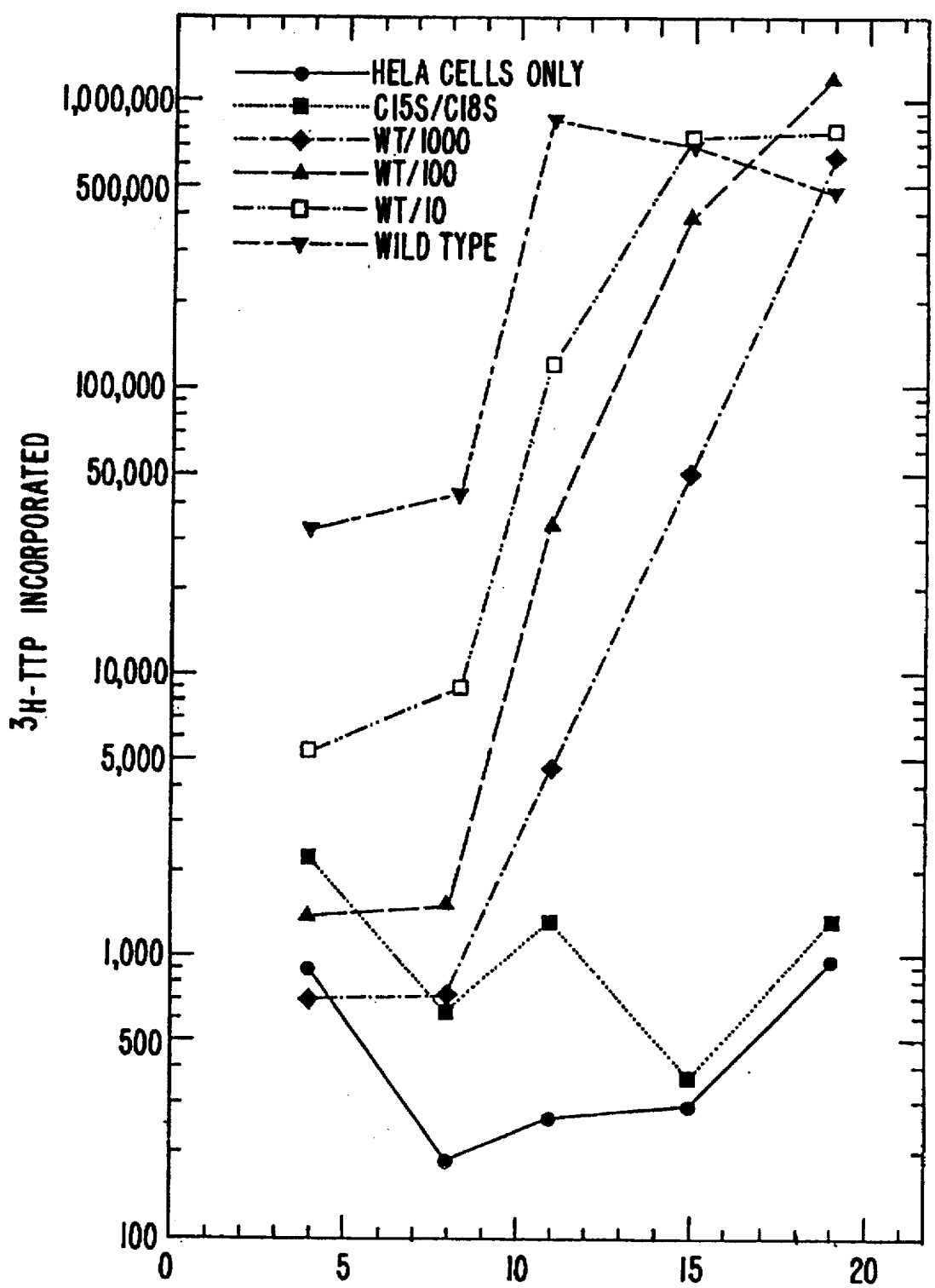
FIG. 6. Endpoint dilution assay of wild type and the C15S/C18S mutant. One mL of clarified supernatants from Hela cells transfected with the respective clones were treated as in FIG. 5. The wild type viral supernatant was also diluted 10, 100, and 1000 fold with media; the C15S/C18S mutant was undiluted. On the days indicated, samples were removed, clarified and tested for the presence of reverse transcriptase activity. The samples and dilutions tested are indicated on the figure.

The infectious potential of these mutants was assayed by taking clarified supernatants from the transfected HeLa cells, adjusting them for equal reverse transcriptase activities, and incubating them with H-9 cells for 12 hours in the presence of 2 µg/mL polybrene. The H-9 cells were carried as usual with the addition of 2 µg/mL polybrene. The production of virus was determined by following reverse transcriptase activity over time. Supernatants from HeLa cells transfected with the wild type clone, contained infectious virus as demonstrated by a rise in H9 cell supernatant RT activity, five days post-infection (see FIG. 5). Supernatants from HeLa cells transfected with the mutant HIV-1 clones produced virus that was not infectious as determined by this analysis. Even after 32 days, Hela supernatants containing mutant virus failed to induce RT activity in H9 cells. Similar cultures were analyzed 44 days post-infection, and the mutant viruses still showed no indication of infection. The same results were seen when these supernatants were applied to human peripheral blood lymphocytes. An endpoint dilution assay indicates that the mutants are at least 1000, and possibly even 10,000 times less infectious than an identical amount of wild type virus (based upon reverse transcriptase activities). As shown in FIG. 6, wild type virus from Hela cell culture fluids, even after being diluted 1000 fold, is still able to productively infect H9 cells and human PBLs. Undiluted mutant, C15S/C19S, is still unable to productively infect H9 cells or human PBLs.

Figure 7:
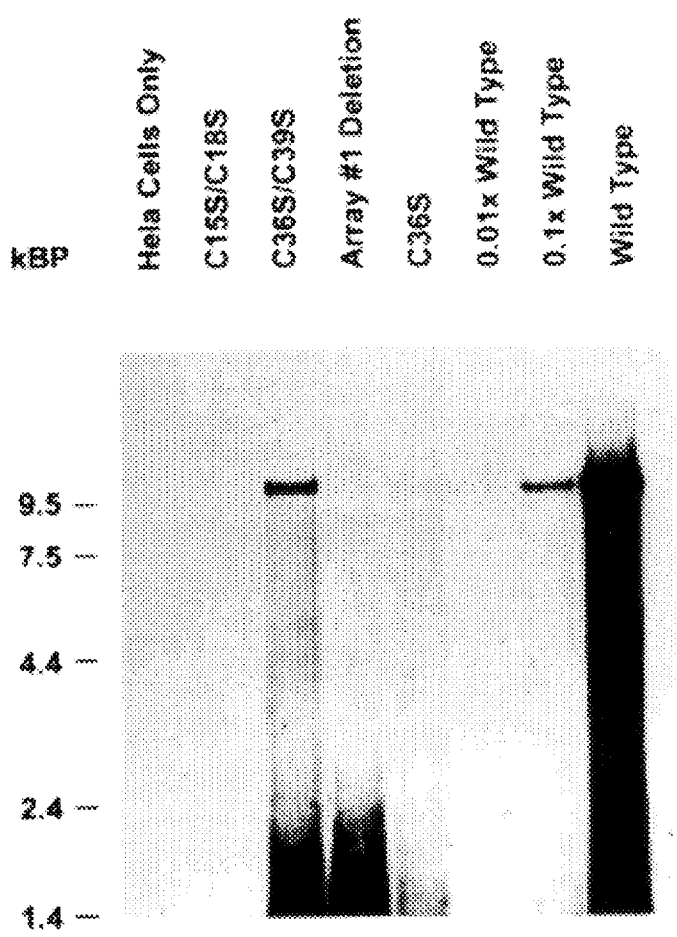
FIG. 7. Northern analysis of mutant and wild type HIV-I viral RNA. Supernatants were treated as described in FIG. 4 and processed for Northern analysis. A nick translated, full length HIV-I clone was used to probe for genomic RNA. Samples are as indicated on the figure.

In an attempt to detect RNA in these mutants, Northern analysis was performed on the supernatants. The samples were adjusted for equal amounts RT activity, as judged by the $^3$H-TTP incorporation data (see Table 8 above). Viral RNA was isolated and separated by electrophoresis on a formaldehyde gel. The RNA was then transferred onto nitrocellulose and probed with a complete HIV-1 nick translated probe. As can be seen in FIG. 7, wild type virus had a correct size band which corresponded to 9.7 kBP. The mutant virions, contained reduced amounts of genomic RNA when compared to an equal amount of wild type virus. From a 1/10 and 1/100 dilution of wild type virus, both of which are detected on the exposed Northern film, the C15S/C18S, array #1 deletion, and the C36s mutants contained approximately 2–5% the amount of genomic RNA contained in the same amount of wild type HIV-I particles, and the C36S/C39S mutant contained about 20% of the RNA found in wild type. It is very interesting to note that the mutants are still non-infectious, even though they have a 5-20% genomic RNA content when compared to an equal number of wild type particles. Thus, while the lack of infectivity of the mutants may be due in part to the absence of viral RNA, the results suggest that there is an additional role that is performed by this conserved cysteine array in the nucleocapsid protein, and that this function is also sensitive to these alterations. This observation has also been made in the Moloney-MuLV mutants.

As shown by the above experiments, alteration of either of the two conserved cysteine arrays of HIV-1 results in non-infectious virions, phenotypically similar to those seen in Mo-MuLV which contains only one conserved array. Thus, both arrays are believed to be required for efficient recognition and packaging of homologous genomic RNA.

As has been shown, it is possible to uncouple virus assembly, budding and maturation from complexation with viral RNA by alteration of the invariant residues of arrays. It is concluded that any method of altering the chemical or biological properties of these residues will result in the production of non-infectious virus. Thus, any reagent or combination of reagents that specifically alters the biological function of these invariant residues could form the basis for the design of effective therapeutic and/or prophylactic procedures for any retrovirus.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit of and scope of the invention.

What is claimed is:

1. A method of reducing the infectivity of a retrovirus consisting essentially of introducing at least one mutation in a cysteine array present in the nueleocapsid domain of the gag precursor polyprotein of said virus, wherein a portion of the array is present after introducing said mutation, said cysteine array having the sequence -Cys-X-X-Cys-X-X-X-X-His-X-X-X-X-Cyswherein X represents variable amino acids.

2. The method of claim 1, wherein said mutation is such that the infectivity of said retrovirus is reduced by at least 3 orders of magnitude as measured by an infectivity assay.

3. The method of claim 2, wherein said mutation is such that the infectivity of said retrovirus is reduced by at least 5 orders of magnitude as measured by an infectivity assay.

4. The method of claim 1, wherein said mutation is such that said retrovirus is rendered non-infective as measured by an infectivity assay.

5. The method of claim 1, wherein said mutation is an invariant residue of said sequence.

6. The method of claim 1, wherein said mutation is a variant residue of said sequence.

7. The method of claim 1, wherein said retrovirus is human immunodeficiency virus (HIV).

8. The method of claim 7, wherein said retrovirus is human immunodeficiency virus 1 (HIV-1).

9. The method of claim 8, wherein said at least one mutation is present in two of said cysteine arrays.

10. The method of claim 8, wherein said mutation is an invariant residue of said sequence.

11. The method of claim 8, wherein said mutation is a variant residue of said sequence.

12. The method of claim 8, wherein said cysteine at positions 1 and 4 of said array are replaced.

13. The method of claim 8, wherein said cysteine at position 1 of said array is replaced.

14. The method of claim 8, wherein at least one said mutation is a deletion mutation.

15. A non-infectious mutant of an infectious retrovirus comprising a form of said infectious retrovirus having a mutation in a cysteine array present in the nucleocapsid domain of the gag precursor polyprotein of said infectious retrovirus, said cysteine array having the sequence -Cys-X-X-Cys-X-X-X-X-His-X-X-X-X-Cyswherein X represents variable amino acids.

16. The non-infectious mutant of claim 15, wherein said infectious retrovirus is human immunodeficiency virus (HIV).

17. The non-infectious mutant of claim 16, wherein said infectious retrovirus is human immunodeficiency virus 1 (HIV-1).

18. The method of claim 1, wherein said mutation is a single point mutation.

* * * * *